(12) United States Patent
Honma et al.

(10) Patent No.: US 10,551,323 B2
(45) Date of Patent: *Feb. 4, 2020

(54) PLASMA SPECTROSCOPY ANALYSIS METHOD

(71) Applicant: ARKRAY, Inc., Kyoto (JP)

(72) Inventors: Kojiro Honma, Kyoto (JP); Kentaro Kiriyama, Kyoto (JP); Hirofumi Yamada, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,482

(22) Filed: Jul. 2, 2018

(65) Prior Publication Data

US 2019/0011370 A1 Jan. 10, 2019

(30) Foreign Application Priority Data

Jul. 5, 2017 (JP) .................................. 2017-131942

(51) Int. Cl.
  *G01J 3/30* (2006.01)
  *G01N 21/73* (2006.01)
  *G01N 1/28* (2006.01)

(52) U.S. Cl.
  CPC .............. *G01N 21/73* (2013.01); *G01N 1/28* (2013.01); *G01N 2001/2893* (2013.01)

(58) Field of Classification Search
  CPC ........ G01N 33/493; G01N 33/20; G01N 1/38; G01N 21/25; G01N 21/66; G01N 21/67; G01N 21/69; G01N 21/73; G01J 3/443
  USPC ........................................................ 356/315
  See application file for complete search history.

(56) References Cited

U.S. PATENT DOCUMENTS

| | | | | |
|---|---|---|---|---|
| 4,531,836 A | * | 7/1985 | Smith, Jr. | ................. G01J 3/32 356/316 |
| 4,893,259 A | | 1/1990 | Grosser et al. | |
| 2003/0168132 A1 | * | 9/2003 | Nagasawa | .............. G01N 15/02 148/508 |
| 2007/0019182 A1 | * | 1/2007 | Grodzins | ........... G01N 21/1702 356/72 |
| 2013/0267035 A1 | * | 10/2013 | Russo | .................... G01N 21/75 436/171 |

(Continued)

FOREIGN PATENT DOCUMENTS

JP 2016-130734 A 7/2016

OTHER PUBLICATIONS

Extended European Search Report issued in corresponding European Patent Application No. 18180928.6 dated Sep. 18, 2018.

*Primary Examiner* — Tarifur R Chowdhury
*Assistant Examiner* — Jonathon Cook
(74) *Attorney, Agent, or Firm* — Morgan, Lewis & Bockius LLP

(57) ABSTRACT

The disclosure provides plasma spectroscopy analysis methods using a preparatory process of adding a control metal species that is different from an analyte metal species to a sample so as to have a known concentration; a concentration process of introducing the sample to a measurement container, and applying an electric current across a pair of electrodes disposed in the measurement container to concentrate the analyte metal species and the control metal species in the sample in a vicinity of at least one of the electrodes; a detection process; a correction process; and a quantification process.

20 Claims, 21 Drawing Sheets

(56) References Cited

U.S. PATENT DOCUMENTS

2016/0202187 A1    7/2016  Shiraki et al.
2016/0282329 A1*   9/2016  Uwabu ................ G01N 33/493

* cited by examiner

PLASMA SPECTROSCOPY ANALYSIS METHOD

CROSS-REFERENCE TO RELATED APPLICATION

This application claims priority under 35 USC 119 from Japanese Patent Application No. 2017-131942, filed on Jul. 5, 2017, the disclosure of which is incorporated by reference herein.

BACKGROUND

Technical Field

The present invention relates to a method for quantifying a heavy metal by concentrating the heavy metal at an electrode via stripping and by performing plasma spectroscopy.

Background Art

A method for quantifying heavy metal ions in a sample is disclosed in JP 2016-130734 A, in which the heavy metal ions in a sample are concentrated at an electrode via stripping, a large electric current is subsequently applied such that the heavy metal ions exhibit plasma emission, and the heavy metal ions in the sample are quantified using the amount of emitted light.

SUMMARY

Depending on characteristics and condition of the samples, the samples often exhibit variation in the amount of plasma emission for identical concentrations of heavy metal ions. Quantification accuracy may suffer as a result of such variation in emission amounts. An object of an exemplary embodiment of the present invention is to improve the accuracy of quantification by suppressing such variation in emission amounts.

A plasma spectroscopy analysis method of an exemplary embodiment of the present invention includes a preparatory process, a concentration process, a detection process, a correction process, and a quantification process. In the preparatory process, a control metal species that is different from an analyte metal species is added to a sample so as to have a known concentration. In the concentration process, the sample is introduced to a measurement container, and an electric current is applied across a pair of electrodes disposed in the measurement container to concentrate the analyte metal species and the control metal species present in the sample in a vicinity of at least one of the electrodes. In the detection process, an electric current is applied across the pair of electrodes after the concentration process so as to generate plasma, and emitted light from the analyte metal species and the control metal species arising due to the plasma is detected. In the correction process, a corrected value is calculated by correcting an analysis emission amount that is a net emission amount at an analysis wavelength corresponding to the analyte metal species detected in the detection process, using a control emission amount that is a net emission amount at a control wavelength corresponding to the control metal species detected in the detection process. In the quantification process, the analyte metal species in the sample is quantified by comparing the corrected value to a calibration curve obtained by advance measurements of known concentrations of the analyte metal species.

In the plasma spectroscopy analysis method of the exemplary embodiment of the present invention, an analyte metal species is quantified by correcting a plasma emission amount due to the analyte metal species using a plasma emission amount due to a known concentration of a control metal species. The characteristics and state of the sample affect the plasma emission amount of the control metal species. However, the arising plasma emission amount corresponds to the known concentration of the control metal species. Standardizing (for example, "dividing") the plasma emission amount due to the analyte metal species using the plasma emission amount corresponding to the known concentration of the control metal species accordingly enables the effect of the characteristics and state of the sample to be eliminated to the maximum extent. Namely, variation in emission amounts due to the characteristics or state of the sample are suppressed, thereby improving the accuracy of quantification of the analyte metal species when using the plasma spectroscopy analysis method.

BRIEF DESCRIPTION OF DRAWINGS

Exemplary embodiments will be described in detail based on the following figures, wherein.

DETAILED DESCRIPTION

Figure 1A:
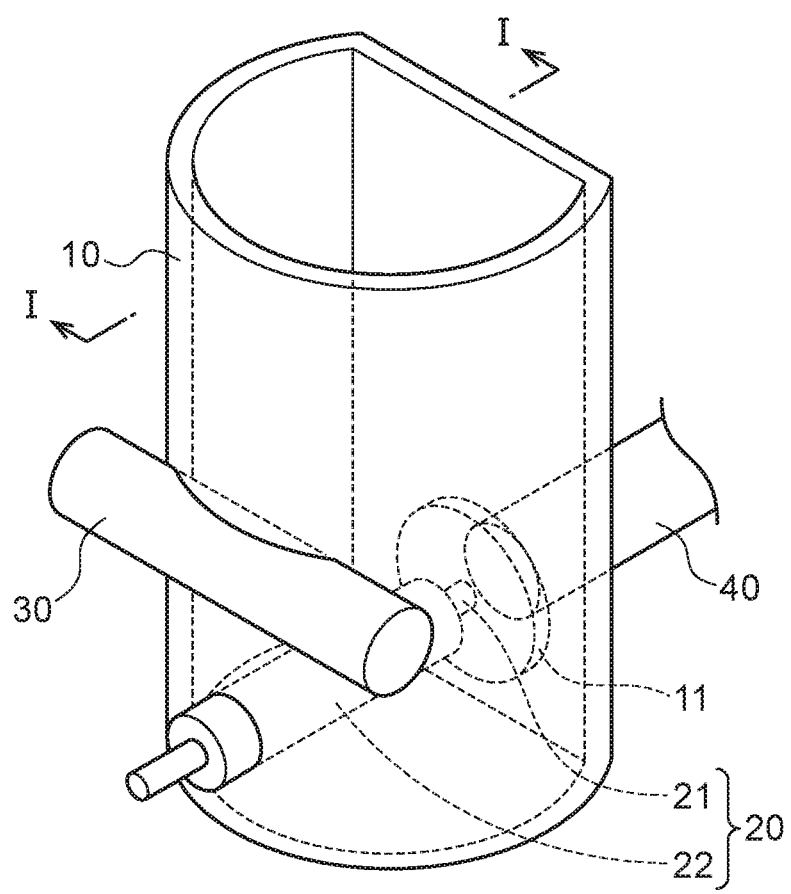
FIG. 1A is a schematic see-through perspective view illustrating relevant portions of a measurement container employed in an exemplary embodiment of the present invention.

As described above, a plasma spectroscopy analysis method of an exemplary embodiment of the present invention includes a preparatory process, a concentration process, a detection process, a correction process, and a quantification process. In the preparatory process, a control metal species that is different from an analyte metal species is added to a sample so as to have a known concentration. In the concentration process, the sample is introduced to a measurement container, and an electric current is applied across a pair of electrodes disposed in the measurement container to concentrate the analyte metal species and the control metal species present in the sample in a vicinity of at least one of the electrodes. In the detection process, an electric current is applied across the pair of electrodes after the concentration process so as to generate plasma, and emitted light from the analyte metal species and the control metal species arising due to the plasma is detected. In the correction process, a corrected value is calculated by correcting an analysis emission amount that is a net emission amount at an analysis wavelength corresponding to the analyte metal species detected in the detection process, using a control emission amount that is a net emission amount at a control wavelength corresponding to the control metal species detected in the detection process. In the quantification process, the analyte metal species in the sample is quantified by comparing the corrected value to a calibration curve obtained by advance measurements of known concentrations of the analyte metal species.

The plasma spectroscopy analysis method according to the present exemplary embodiment quantifies the analyte metal species using a emission amount from plasma emission. A liquid sample is introduced to a measurement container in which a pair of electrodes are disposed. First, a predetermined electric current is applied across the electrodes (which is referred to as "stripping") to concentrate an analyte metal species in the vicinity of one of the electrodes. Thereafter, for example, a larger electric current than that employed in the stripping is applied in order to cause plasma emission from the concentrated analyte metal species.

The preparatory process is a process in which a control metal species that is different from the analyte metal species is added to the sample so as to have a known concentration.

Here, the sample is a liquid. However, the sample may be a dilute solution in which a solid is suspended, dispersed, or dissolved in a liquid medium. The liquid sample may, for example, employ a stock solution of the sample as it is, or, if the concentration of the stock solution is too high, a dilute solution in which stock solution is, for example, suspended, dispersed, or dissolved in a liquid medium may be employed. The medium for the liquid is not particularly limited so long as it is capable of suspending, dispersing, or dissolving the sample. Examples thereof include water or a buffering solution. The sample may be a biological organism sample (or specimen), an environmental sample (or specimen), a metal, a chemical, or a pharmaceutical product. Biological samples are not particularly limited, and examples thereof include urine, blood, hair, saliva, sweat, and nails. Blood samples include, for example, red blood cells, whole blood, blood serum, and blood plasma. Examples of biological organisms include humans, non-human animals, and plants. Examples of non-human animals include mammals other than humans, amphibians, reptiles, fish, and insects. Environmental samples are not particularly limited, and examples thereof include food products, water, soil, and air or other atmospheric gases. Examples of food products include fresh food products and processed food products. Examples of water include drinking water, groundwater, river water, seawater, and sewage water.

The pH, for example, of liquid sample may be regulated. The value of such pH is not particularly limited so long as it assists detection of an analyte. For example, the pH value of the liquid sample may be regulated using a pH regulating reagent such as an alkali reagent or an acidic reagent.

Examples of alkali reagents include alkalis and aqueous solutions of alkalis. Such alkalis are not particularly limited, and examples thereof include sodium hydroxide, lithium hydroxide, potassium hydroxide, and ammonia. Examples of aqueous solutions of alkalis include an alkali that is diluted in water or a buffer solution. The concentration of the alkali in such an alkali aqueous solution is not particularly limited, and may, for example, be from 0.01 mol/L to 5 mol/L.

Examples of acidic reagents include acids and aqueous solutions of acids. Such acids are not particularly limited, and examples thereof include hydrochloric acid, sulfuric acid, acetic acid, boric acid, phosphoric acid, citric acid, malic acid, succinic acid, and nitric acid. Examples of aqueous solutions of acids include an acid that is diluted in water or a buffer solution. The concentration of the acid in such an acidic aqueous solution is not particularly limited, and may, for example, be from 0.01 mol/L to 5 mol/L.

The analyte metal species is not particularly limited so long as it can exist in a charge-carrying state, for example an ionized state, in the liquid sample. Examples of the analyte metal species include aluminum (Al), antimony (Sn), arsenic (As), barium (Ba), beryllium (Be), bismuth (Bi), cadmium (Cd), cesium (Cs), gadolinium (Gd), lead (Pb), mercury (Hg), nickel (Ni), palladium (Pd), platinum (Pt), tellurium (Te), thallium (Tl), thorium (Th), tin (Sn), tungsten (W), and uranium (U). It is preferable that only one kind of analyte metal species be present in the sample. However, as long as the characteristic peaks seen in the emission spectra differ in wavelength (analysis wavelength) and it is possible to distinguish between these peaks in emission spectra, two kinds or more of analyte metal species may be present.

The liquid sample may, for example, include a reagent to separate out the analyte metal species in the sample. Examples of reagents include chelating agents and masking agents. Examples of chelating agents include dithizone, tiopronin, meso-2,3-dimercaptosuccinic acid (DMSA), sodium 2,3-dimercapto-1-propanesulfonic acid (DMPS), ethylenediaminetetraacetic acid (EDTA), nitrilotriacetic acid (NTA), ethylenediamine-N,N'-disuccinic acid (EDDS), and α-lipoic acid. In the present analysis method, "masking" refers to inactivating SH-groups, and may, for example, be performed by chemically modifying SH-groups. Examples of masking agents include maleimide, N-methylmaleimide, N-ethylmaleimide, N-phenylmaleimide, maleimidopropionic acid, iodoacetamide, and iodoacetate.

The control metal species is a metal species that is different from the analyte metal species, and is not particularly limited as long so it can exist in a charge-carrying state, for example an ionized state, in the liquid sample, and is preferably a metal species capable of generating plasma emission such as a metal species selected from the group consisting of zinc (Zn), cadmium (Cd), silver (Ag), gold (Au), mercury (Hg), thallium (Tl), lead (Pb), and indium (In). It is preferable that only one kind of control metal species be present in the sample. However, as long as the characteristic peaks seen in the emission spectra differ in wavelength (control wavelength) and it is possible to distinguish between these peaks in emission spectra, two kinds or more or control metal species may be present. Moreover, it is preferable that a characteristic peak of a control metal species exhibited at a control wavelengths in an emission spectrum can be distinguished from an analysis wavelength corresponding to a peak for an analyte metal species. For example, in a case in which the analyte metal species is mercury or lead, the control metal species is preferably thallium. In other words, it is sufficient that the analyte metal species and the control metal species are configured by a combination of substances that both have detectable plasma emission, and that have an analysis wavelength and a control wavelength that differ from each other.

The control metal species is added to the sample so as to be a known concentration. The known concentration is not particularly limited so long as it is a concentration that does not affect detection of an analyte metal species assumed to be contained in the sample, and is a concentration at which the control metal species can be adequately detected. It is, for example, preferable that the control metal species may be added such that its final concentration in the sample is 100 ppb.

The concentration process is a process in which the sample is introduced to the measurement container and an electric current is applied across the pair of electrodes disposed in the measurement container so as to concentrate the analyte metal species and the control metal species in the sample in the vicinity of at least one of the electrodes.

The "pair of electrodes" refers to a combination of a cathode and an anode in electrolysis. The electrodes are solid electrodes, and specifically, may be rod electrodes or the like. The electrode material is not particularly limited, and any appropriate solid electrically conductive material may be employed therefor according to the analyte metal species and the control metal species. The electrode material may, for example, be a nonmetal, may be a metal, or may be a mixture of a nonmetal and a metal. In a case in which the electrode material includes a nonmetal, the electrode material may, for example, include one type of nonmetal, or may include two or more types of nonmetal. Carbon is an example of a nonmetal. In a case in which the electrode material includes a metal, the electrode material may, for example, include one type of metal, or may include two or more types of metal. Examples of metals include gold, platinum, copper, zinc, tin, nickel, palladium, titanium, molybdenum, chromium, and iron. In a case in which the electrode material includes two or more types of metal, the electrode material may be an alloy. Examples of alloys include brass, steel, Inconel (registered trademark), nichrome, and stainless steel. The pair of electrodes may, for example, both be formed from the same material, or may be formed from different materials from each other.

The size of the electrodes is not particularly limited so long as they are at least partially housed inside the measurement container. Note that it is preferable for the size of the measurement container to be as small as possible if attempting to produce a cartridge type measurement container suitable for mass production. In such cases, the electrodes are also made smaller so as to correspond to the size of the measurement container. Moreover, one or both of the pair of electrodes may be pre-installed as a unit in the measurement container, or alternatively, the electrodes may be inserted into the measurement container as appropriate when a measurement is to be taken.

The one electrode is the electrode where the analyte metal species and the control metal species are concentrated, and is the cathode in this case.

As described above, the concentration process is a process in which, in the presence of the sample, an electric current is applied across the pair of electrodes to concentrate the analyte metal species and the control metal species in the sample in the vicinity of the one electrode. The pair of electrodes are in contact with the sample. In the concentration process, the "vicinity of the one electrode" is not particularly limited, and may for example be a range over which plasma is generated in the detection process, described later, such as the surface of the one electrode.

In the concentration process, for example, a portion of the analyte metal species and the control metal species in the sample may be concentrated in the vicinity of the one electrode, or the entirety of the analyte metal species and the control metal species in the sample may be concentrated in the vicinity of the one electrode.

In the concentration process, charge conditions of the pair of electrodes are preferably set such that the electrode employed in detection of the analyte metal species and the control metal species in the detection process described below, namely the electrode where plasma is generated (also referred to hereafter as the "plasma generating electrode") is the one electrode, and the analyte metal species and the control metal species are concentrated at this electrode. Regarding the charging conditions, the direction of the electric current should be set such that the one electrode (namely, the plasma generating electrode) is a cathode in the concentration process, since the analyte metal species and the control metal species are normally metal ions carrying a positive charge.

The concentration of the analyte metal species and the control metal species may, for example, be regulated by voltage. Accordingly, a person skilled in the art is capable of setting an appropriate voltage to cause concentration (also referred to hereafter as a "concentration voltage"). The concentration voltage is, for example, at least 1 mV, and is preferably at least 400 mV. The upper limit of the concentration voltage is not particularly limited. The concentration voltage may, for example, be constant, or may fluctuate. The concentration voltage may, for example, be a voltage at which plasma is not generated.

The application duration of the concentration voltage is not particularly limited, and may be set as appropriate according to the concentration voltage. The application duration of the concentration voltage is, for example, from 0.2 minutes to 40 minutes, and is preferably from 5 minutes to 20 minutes. The voltage may, for example, be applied across the pair of electrodes continuously, or may be applied across the pair of electrodes intermittently. Pulsed application is an example of an intermittent voltage application. In a case in which the application of the concentration voltage is intermittent, the application duration of the concentration voltage may be the total duration over which the concentration voltage is being applied, or may be the total of the duration over which the concentration voltage is being applied and the duration over which the concentration voltage is not being applied.

The voltage application unit employed to apply the voltage across the pair of electrodes is not particularly limited, and, for example, any known voltage supply device may be employed so long as the predetermined voltage can be applied across the pair of electrodes. In the concentration process, the electric current applied across the pair of electrodes is, for example, set from 0.01 mA to 200 mA, preferably from 10 mA to 60 mA, and more preferably from 10 mA to 40 mA.

As described above, in the detection process, a larger electric current than that applied across the pair of electrodes in the concentration process is applied across the pair of electrodes so as to generate plasma, and light emitted by the analyte metal species and the control metal species arising due to the plasma is detected.

Note that the direction of the electric current in the detection process may be the same as the direction of the electric current in the concentration process. However, it is preferable for the voltage application unit to be formed so as to be capable of switching the direction of the electric current during voltage application such that the direction of the electric current during plasma generation is the opposite direction to the direction of the electric current during concentration of the analyte metal species and the control metal species.

Specifically, since in the concentration process the analyte metal species and the control metal species are positively charged, the direction of the electric current generated by the voltage application unit should be set such that the one electrode, serving as a plasma generating electrode, becomes the anode in the detection process.

The concentration process may run straight on into the detection process, but does not have to run straight on into the concentration process. In the former case, the detection process is performed at the same time as the concentration process ends. In the latter case, the detection process is performed no more than a predetermined duration after the end of the concentration process. The predetermined duration is, for example, from 0.001 seconds to 1,000 seconds after the concentration process, and is preferably from 1 second to 10 seconds after the concentration process.

In the detection process, "plasma generation" refers to substantive plasma generation, and specifically, refers to the generation of plasma that exhibits substantive detectable emission in plasma emission detection. As a specific example, plasma emission is detectable using a plasma emission detector.

The substantive plasma generation may, for example, be regulated by voltage. Accordingly, a person skilled in the art is capable of setting an appropriate voltage to generate plasma exhibiting substantive detectable emission (also referred to hereafter as the "plasma generation voltage"). The plasma generation voltage is, for example, at least 10V, and is preferably at least 100V. The upper limit of the plasma generation voltage is not particularly limited. The voltage at which plasma is generated is, for example, a relatively high voltage in comparison to the voltage at which the concentration occurs. Accordingly, the plasma generation voltage is preferably a higher voltage than the concentration voltage. The plasma generation voltage may, for example, be constant, or may fluctuate.

The application duration of the plasma generation voltage is not particularly limited, and may be set as appropriate according to the plasma generation voltage. The plasma generation voltage application duration is, for example, from 0.001 seconds to 0.02 seconds, and is preferably from 0.001 seconds to 0.01 seconds. The plasma generation voltage may, for example, be applied across the pair of electrodes continuously, or may be applied to the pair of electrodes intermittently. Pulsed application is an example of intermittent application. In a case in which the application of the plasma generation voltage is intermittent, the application duration of the plasma generation voltage may, for example, be the duration of a single application of the plasma generation voltage, may be the total duration over which the plasma generation voltage is being applied, or may be the total of the duration over which the plasma generation voltage is being applied and the duration over which the plasma generation voltage is not being applied.

In the detection process, the generated plasma emission may, for example, be detected continuously, or may be detected intermittently. Detection of the emitted light may be performed by, for example, detecting the presence of emitted light, detecting the intensity of emitted light, detecting a specific wavelength, or detecting a spectrum. The detection of a specific wavelength involves, for example, the detection of a particular wavelength emitted by an analyte during plasma emission. The method of detecting emitted light is not particularly limited, and, for example, a known optical measurement instrument such as a Charge Coupled Device (CCD) or a spectroscope may be employed therefor.

In the detection process, the plasma generation voltage may be applied to the pair of electrodes, using the voltage application unit, at a higher voltage than that employed in the concentration process. It is preferable that the direction in which the electric current flows be opposite to that in the concentration process. In the detection process, since the plasma generation voltage is relatively higher than the concentration voltage, the electric current across the electrodes larger than that in the concentration process. The electric current may, for example, be set from 0.01 mA to 100,000 mA, and is preferably from 50 mA to 2,000 mA.

The emission spectrum obtained due to the plasma emission in the detection process may be expressed as a graph in which emission amounts are plotted against individual wavelengths over a predetermined wavelength range. In the correction process, first, a net emission amount corresponding to the analysis wavelength that is a wavelength in the emission spectrum suitable for quantifying the analyte metal species, is taken as an analysis emission amount, and a net emission amount corresponding to the control wavelength that is a wavelength in the emission spectrum suitable for quantifying the control metal species, is taken as a control emission amount. In the correction process, a corrected value is calculated by correcting the analysis emission amount using the control emission amount.

Note that the net emission amount for the analysis emission amount refers to the emission amount at the analysis wavelength due solely to the presence of the analyte metal species, and is a corrected emission amount in which a peak emission amount as the apparent emission amount at the analysis wavelength is corrected using a base emission amount as a emission amount that is independent of the plasma emission of the analyte metal species.

Moreover, the net emission amount for the control emission amount refers to a emission amount at the control wavelength due solely to the presence of the control metal species, and is a corrected emission amount in which a peak emission amount as the apparent emission amount at the control wavelength is corrected using a base emission amount as a emission amount that is independent of the plasma emission of the control metal species.

A method of determining or computing the base emission amount may be set as appropriate according to the type of graph obtained for the emission spectrum. For example, in the emission spectrum, in a case in which a peak emission amount obtained corresponding to a specific wavelength is a portion rising up from a flat portion of a graph of the emission spectrum, the emission amount of the flat portion may be set as the base emission amount.

Note that in a case in which values for control emission amounts differ between samples containing the control metal species at the same known concentration, although the control emission amounts reflect the same known concentration of the control metal species, the difference between the values is thought to arise due to differences in the states of the samples, such as, for example, differences in the types and concentrations of components present in the solution. Such states of the samples may naturally also be expected to affect the analysis emission amounts of the samples. Thus, it is possible to eliminate the effect of the state of the sample on the analysis emission amount to the maximum extent by correcting an analysis emission amount using a control emission amount that reflects a constant known concentration. In the correction process, the method for correcting the analysis emission amount using the control emission amount should be set as appropriate according to the type of graph obtained for the emission spectrum. For example, a value obtained by dividing the analysis emission amount by the control emission amount may be taken as a corrected value. Consequently, the analyte metal species is quantified according to how many times greater in magnitude the analysis emission amount is than the control emission amount reflecting the known concentration.

The quantification process is a process to quantify the concentration of the analyte metal species in the sample based on the corrected value calculated in the correction process. Note that the concentration of the analyte metal species may, for example, be quantified based on a correlative relationship between corrected values and concentrations of an analyte in solution. Such a correlative relationship may, for example, be defined by a calibration curve obtained by plotting corrected values, obtained by performing each of the aforementioned processes for reference samples in which the analyte metal species is present in known concentrations similarly to the case of the sample, against the concentrations of the analyte metal species in the reference samples. The reference samples are preferably a dilution series for the analyte metal species. Defining such a calibration curve enables reliable quantification.

In the plasma spectroscopy analysis method of the present invention, the pair of electrodes may be disposed inside a measurement container that includes a transparent section. In such cases, in the detection process, light emitted by the analyte metal species and the control metal species can be detected by a light receptor disposed so as to be capable of receiving the emitted light through the transparent section.

Explanation follows regarding an example of the measurement container employed in an exemplary embodiment of the plasma spectroscopy analysis method of the present invention, with reference to the drawings. In the drawings, the structure of each section may be simplified as appropriate for ease of explanation. The relative dimensions of the respective sections are schematic and may not be true to reality.

Figure 1B:
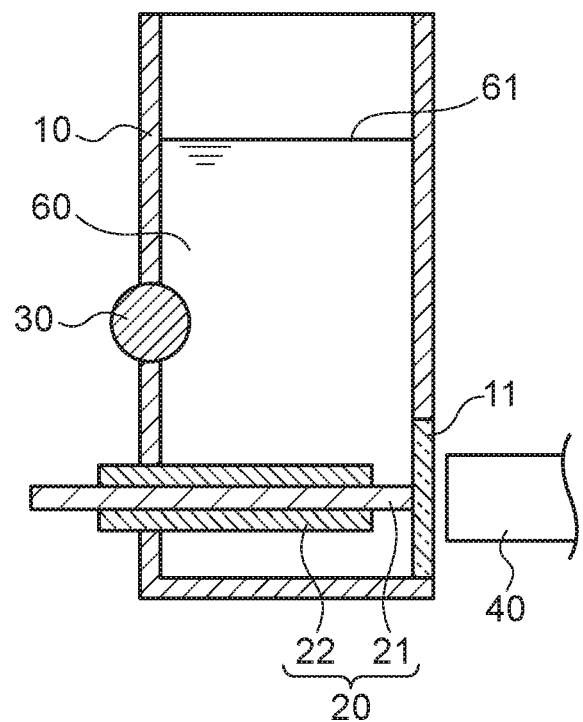
FIG. 1B is a schematic cross-section as viewed along the direction indicated by I-I in FIG. 1A.

FIG. 1A is a schematic see-through perspective view illustrating a measurement container 10 employed in the present exemplary embodiment. FIG. 1B is a schematic cross-section viewed along the direction indicated by I-I in FIG. 1A. As illustrated in FIG. 1A and FIG. 1B, the measurement container 10 employed in the present exemplary embodiment includes a pair of internal electrodes (a plasma generating electrode 20 and a non-plasma generating electrode 30). The measurement container 10 has a substantially circular cylinder shape with part of one side having a planar shape as if it is cut away. This planar portion includes a circular transparent section 11. A light receptor 40 is disposed at the exterior of the measurement container 10 so as to be capable of receiving light emitted by the analyte metal species and the control metal species, via the transparent section 11, when light is generated by applying an electric current across the plasma generating electrode 20 and the non-plasma generating electrode 30. Moreover, the plasma generating electrode 20 is disposed parallel to a liquid surface 61 of a liquid sample 60, and a leading end of the plasma generating electrode 20 is disposed to contact the transparent section 11. Part of a side face of the circular cylinder shaped non-plasma generating electrode 30 is disposed on the side face of the measurement container 10 at a side opposing the transparent section 11 so as to intersect a vertical direction at a right angle, and part of the non-plasma generating electrode 30 is exposed to the interior of the measurement container 10. Namely, a length direction of the non-plasma generating electrode 30 and a length direction of the plasma generating electrode 20 are positioned so as to be twisted with respect to one another. The plasma generating electrode 20 is covered by an insulator 22. The sample 60 that contains the analyte metal species and the control metal species is introduced into the measurement container 10 so as to make contact with the plasma generating electrode 20 and the non-plasma generating electrode 30.

In the present exemplary embodiment, the majority of the surface of the plasma generating electrode 20 is covered by the insulator 22. A portion that is not covered by the insulator 22 is a liquid-contacting portion 21.

In the present exemplary embodiment, the plasma generating electrode 20 and the transparent section 11 contact each other. However, there is no limitation to such a configuration, and, for example, the plasma generating electrode 20 may be disposed at a separation from the transparent section 11. The distance between the plasma generating electrode 20 and the transparent section 11 is not particularly limited, and may, for example, be from 0 cm to 0.5 cm.

The material of the transparent section 11 is not particularly limited, and so long as it is a material that allows light generated by applying an electric current across the plasma generating electrode 20 and the non-plasma generating electrode 30 to pass therethrough, for example, may be set as appropriate according to the wavelengths of the generated light. Examples of materials for of the transparent section 11 include quartz glass, acrylic resin (PMMA), borosilicate glass, polycarbonate (PC), a cyclic olefin polymer (COP), and polymethylpentene (TPX (registered trademark)). The size of the transparent section 11 is not particularly limited, and may be set to a size that allows light generated by applying an electric current across the plasma generating electrode 20 and the non-plasma generating electrode 30 to pass therethrough.

In the present exemplary embodiment, the measurement container 10 has a bottomed circular cylinder shape with part of one side having a planar shape as if it is cut away along the length direction. However, the shape of the measurement container 10 is not particularly limited, and may be any desired shape. The material of the measurement container 10 is not particularly limited, and examples thereof include acrylic resin (PMMA), polypropylene (PP), polyethylene (PE), polyvinyl chloride (PVC), polyethylene terephthalate (PET), and polystyrene (PS). In a case in which the measurement container 10 has a bottomed cylinder shape, the diameter of the measurement container 10 is, for example, from 0.3 cm to 1 cm and the height of the measurement container 10 is, for example, from 0.9 cm to 5 cm. The sample 60 of 0.3 $cm^3$ to 0.8 $cm^3$ is introduced to the measurement container 10.

The light receptor 40 is not particularly limited, and may, for example, be a known optical measurement instrument such as a CCD or a spectroscope. The light receptor 40 may also, for example, be a transmission section that transmits the emitted light to an optical measurement instrument. Examples of transmission sections include a transmission path such as an optical fiber.

The manufacturing method of the measurement container 10 is not particularly limited. For example, a molded body may be manufactured by injection molding, or the measurement container 10 may be manufactured by forming a recess in a substrate such as a plate. Otherwise, the manufacturing method of the measurement container 10 is not particularly limited, and for example, lithography or machining methods may also be employed.

Explanation follows regarding an overview of the plasma spectroscopy analysis method of the present exemplary embodiment, in which metal ions (for example, mercury ions or lead ions) as the analyte metal species are assumed to be present in the aqueous solution of the sample 60.

Figure 2A:
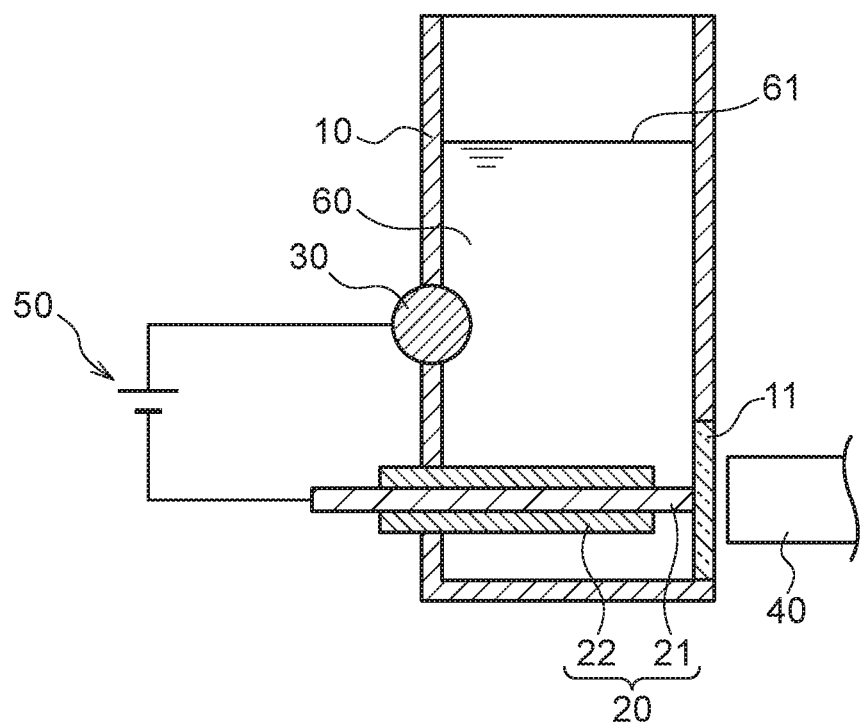
FIG. 2A is a schematic cross-section for giving an overview of a concentration process of plasma spectroscopy analysis employing the measurement container illustrated in FIG. 1A.

First, a known concentration of the control metal species (for example, thallium ions) is added to the sample 60. Then, in a state in which the sample 60 is introduced to the measurement container 10, in the concentration process, as illustrated in FIG. 2A, a voltage application section 50 is used to apply a voltage with the plasma generating electrode 20 serving as a cathode and the non-plasma generating electrode 30 serving as an anode. Then, the metal ions present in the sample 60 are drawn toward the liquid-contacting portion 21 of the plasma generating electrode 20 as the cathode.

Figure 2B:
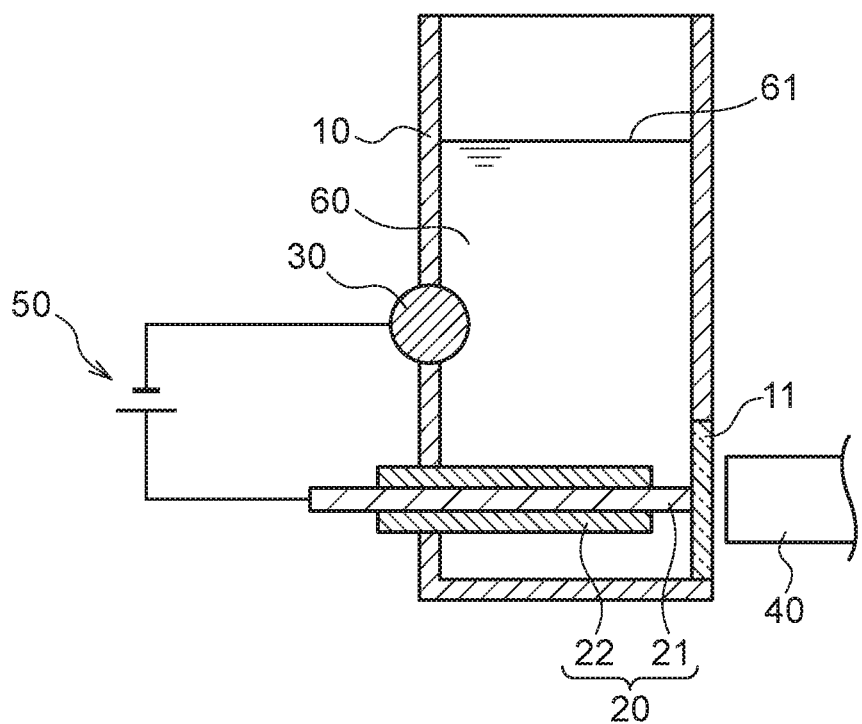
FIG. 2B is a schematic cross-section for giving an overview of a detection process.

Next, in the detection process, as illustrated in FIG. 2B, the voltage application section 50 is used to apply a voltage but with the plasma generating electrode 20 serving as an anode and the non-plasma generating electrode 30 serving as a cathode. Then, plasma emission is generated by the metal ions drawn to the vicinity of the liquid-contacting portion 21 of the plasma generating electrode 20 in the preceding concentration process. This plasma emission passes through the transparent section 11 and is received and detected by the light receptor 40.

Figure 3:
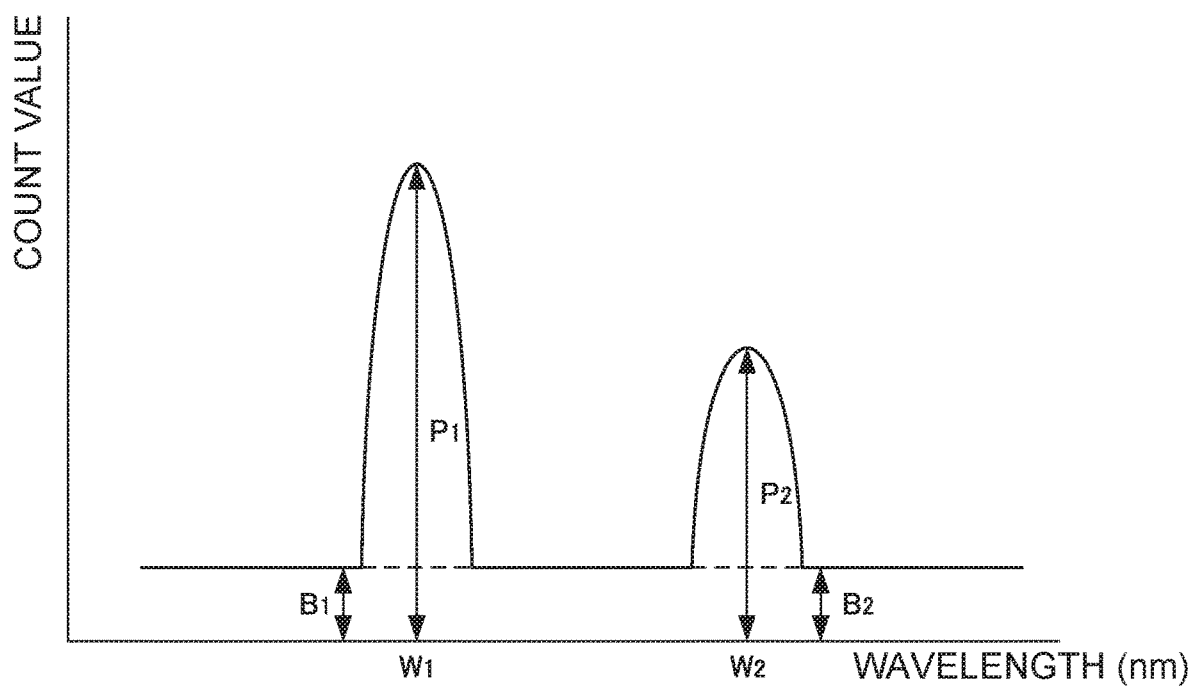
FIG. 3 is a schematic diagram illustrating an emission spectrum obtained in a detection process.

Suppose that an emission spectrum obtained in the detection process is as illustrated in FIG. 3. Note that in FIG. 3, $W_1$ is the analysis wavelength, $W_2$ is the control wavelength, $P_1$ is the peak emission amount at the wavelength $W_1$, $P_2$ is the peak emission amount at the wavelength $W_2$, $B_1$ is the base emission amount corresponding to the peak emission amount $P_1$, and $B_2$ is the base emission amount corresponding to the peak emission amount $P_2$. The magnitude relationships between $W_1$ and $W_2$, and between $P_1$ and $P_2$, are not limited to those illustrated. Moreover, although $B_1$ and $B_2$ are illustrated as if they were the same values as each other, there is no limitation thereto, and configurations in which one is a greater value than the other are also possible.

In such a case, an analysis emission amount $E_1$ of the analyte metal species may, for example, be defined as in the following equation:

$$E_1=(P_1-B_1)/B_1=P_1/B_1-1$$

Moreover, a control emission amount $E_2$ of the control metal species may be similarly defined as in the following equation:

$$E_2=(P_2-B_2)/B_2=P_2/B_2-1$$

Then, a corrected value C may be defined as in the following equation:

$$C=E_1/E_2$$

As above, the analysis emission amount $E_1$ as the net emission amount is defined by how many times greater the value obtained by subtracting the base emission amount $B_1$ from the peak emission amount $P_1$ ($P_1-B_1$) is than the base emission amount $B_1$. However, there is no limitation to such a definition. For example, the analysis emission amount $E_1$ may be defined as a value obtained by subtracting the base emission amount $B_1$ from the peak emission amount $P_1$ ($P_1-B_1$), or may be defined by how many times greater the peak emission amount $P_1$ is than the base emission amount $B_1$ (namely, $P_1/B_1$). Similar applies in the case of the control emission amount $E_2$ described above. For example, out of the above definitions, the definition that obtains the calibration curve with the highest regression coefficient may be adopted.

EXAMPLES (1) Plasma Spectroscopy Analysis

The emission amount of mercury or lead was measured using plasma spectroscopy analysis in the following manner using the measurement container.

Namely, in the preparatory process, 8 µL of a 10 ppm aqueous solution of thallous acetate was dissolved in 776 µL of urine samples (#1 to #18) and a blank sample (sample #0) containing neither mercury nor lead. The concentration of thallous acetate in the urine samples thus became approximately 100 ppb. In this state, 500 µL of each urine sample was taken up into a 1.5 mL Eppendorf tube, and 41.9 mg of lithium hydroxide was then added, followed by agitation for five minutes using a vortex mixer. Then, 25 µL of ethanol was added and mixed, and 420 µL of the resulting mixture was introduced into the measurement container 10.

Then, in the concentration process, an electric current was applied under the following concentration conditions, with the plasma generating electrode 20 serving as the cathode and the non-plasma generating electrode 30 serving as the anode, thereby concentrating positive metal ions in the vicinity of the plasma generating electrode 20. Note that the applied electric current was a constant current and the applied voltage fluctuated in response to the resistance of the urine sample.

Concentration Conditions
Applied electric current: 20 mA
Pulse period: 4 seconds
Duty (pulse ratio): 50%
Application duration: 600 seconds Immediately after the concentration process, in the detection process, a voltage was applied under the following detection conditions but with the plasma generating electrode 20 serving as the anode and the non-plasma generating electrode 30 serving as the cathode. The emission intensity (count value) at each wavelength of the generated plasma emission was measured. Note that the applied voltage was a constant voltage, and the applied electric current fluctuated in response to the resistance of the urine sample. The applied electric current was of a greater value than the electric current applied under the concentration conditions.

Figure 4A:
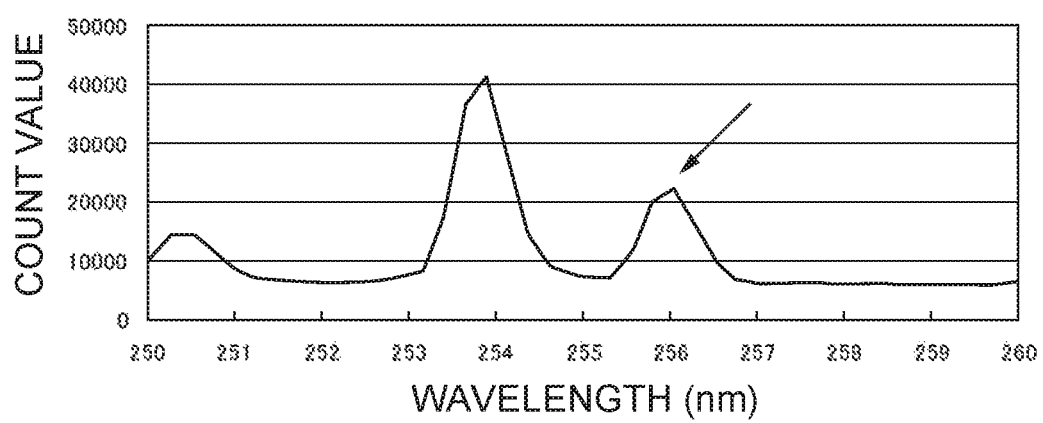
FIG. 4A illustrates an emission spectrum for mercury.
Figure 4B:
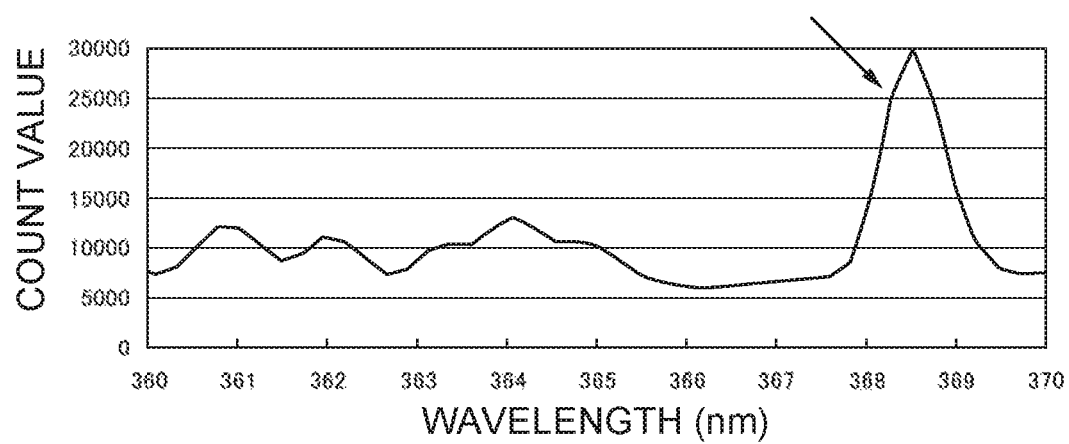
FIG. 4B illustrates an emission spectrum for lead.

Detection Conditions
Applied voltage: 500 V
Pulse period: 50 µs
Duty: 50%
Application duration: 2.5 ms Note that values obtained by dividing the count values of the characteristic peak for mercury at the 256 nm wavelength (see FIG. 4A) and the characteristic peak for lead at the 368 nm wavelength (see FIG. 4B) by the background count value were respectively taken as the Hg analysis emission amount ($h_0$) and the Pb analysis emission amount ($p_0$). Values obtained by dividing the count values of the characteristic peaks for thallium at the 276 nm wavelength and the 351 nm wavelength by the background count value were respectively taken as a control emission amount (276) ($t_1$) and a control emission amount (351) ($t_2$).

In the correction process, a value obtained by dividing the Hg analysis emission amount ($h_0$) by the control emission amount (276) was calculated as an Hg corrected value (276) ($h_1$), and a value obtained by dividing the Hg analysis emission amount ($h_0$) by the control emission amount (351) was calculated as an Hg corrected value (351) ($h_2$). Similarly, a value obtained by dividing the Pb analysis emission amount ($p_0$) by the control emission amount (276) was calculated as a Pb corrected value (276) ($p_1$), and a value obtained by dividing the Pb analysis emission amount ($p_0$) by the control emission amount (351) was calculated as a Pb corrected value (351) ($p_1$).

(2) Reference Measurement

Mercury reference measurements were taken using a direct thermal decomposition mercury analyzer (MA-3000, manufactured by Nippon Instruments). Namely, 150 µL of distilled water was added to the same 50 µL urine samples as employed in the plasma spectroscopy analysis, and 40 µL of a 1% L-cysteine solution was also added thereto. The resulting mixtures were then respectively placed in the measurement boat of the above analyzer together with one grain of granular activated carbon, and measurements were taken using the above analyzer to obtain Hg reference measurement values ($x_H$).

Lead reference measurements were outsourced to an external organization, in which Pb reference measurement values ($x_P$) were obtained using an inductively coupled plasma analyzer.

(3) Calibration Curve

As to Hg analysis emission amounts ($h_0$), Hg corrected values (276) ($h_1$), and Hg corrected values (351) ($h_2$), by measuring aqueous solutions of mercury chloride at plural known concentrations, approximate curves were derived therefrom in correspondence to the Hg reference measurement values ($x_H$) obtained through the reference measurements of the identical aqueous solutions, and the approximate curves were taken as respective calibration curves. Further, as to Pb analysis emission amounts ($p_0$), Pb corrected values (276) ($p_1$), and Pb corrected values (351) ($p_2$), by measuring aqueous solutions of lead nitrate at plural known concentrations, approximate curves were derived therefrom in correspondence to the Pb reference measurement values ($x_P$) obtained through the reference measurements of the identical aqueous solutions, and the approximate curves were taken as respective calibration curves. The approximate curves were derived as quadratic polynomials in Equation (1) below, in which x is the Hg reference measurement value ($x_H$) or the Pb reference measurement value ($x_P$), and y is the corresponding Hg analysis emission amount ($h_0$), the Hg corrected value (276) ($h_1$) or the Hg corrected value (351) ($h_2$), or the Pb analysis emission amount ($p_0$), the Pb corrected value (276) ($p_1$) or the Pb corrected value (351) ($p_2$).

$$y = ax^2 + bx + c \tag{1}$$

Note that the coefficients in Equation (1) were as shown in Table 1 below.

TABLE 1

| | Coefficient | | |
|---|---|---|---|
| y | a | b | c |
| $h_0$ | −0.00032 | 0.07199 | −0.01178 |
| $h_1$ | −0.000041 | 0.011784 | −0.001795 |
| $h_2$ | −0.000016 | 0.00485 | −0.000722 |
| $p_0$ | −0.00065 | 0.15079 | 0.21538 |
| $p_1$ | −0.00008 | 0.024949 | 0.032814 |
| $p_2$ | −0.000032 | 0.010295 | 0.013196 |

(4) Concentration-Converted Value

The values $h_0$, $h_1$, and $h_2$, and also the values $p_0$, $p_1$, and $p_2$ obtained from the respective sample measurements correspond to the value of y in Equation (1) above. Accordingly, Equation (2) which is a modified form of Equation (1) was used to find x, which is a concentration-converted value (namely, $H_0$, $H_1$ or $H_2$, or $P_0$, $P_1$ or $P_2$).

$$x = [-b + \sqrt{\{b^2 - 4a(c-y)\}}]/(2a) \tag{2}$$

The values described above for mercury and for lead were given as shown in Table 2 and in Table 3, respectively.

TABLE 2

| | Hg | | | | | | | |
|---|---|---|---|---|---|---|---|---|
| | Reference measurement value (ppb) ($X_H$) | Analysis emission amount ($h_0$) | Control emission amount | | Hg corrected value | | Hg concentration-converted value | | |
| | | | (276) ($t_1$) | (351) ($t_2$) | (276) ($h_1 = h_0/t_1$) | (351) ($h_2 = h_0/t_2$) | for $h_0$ ($H_0$) (ppb) | for $h_1$ ($H_1$) (ppb) | for $h_2$ ($H_2$) (ppb) |
| Sample # | | | | | | | | | |
| 0 | 0.00 | −0.01 | 6.56 | 16.32 | −0.002 | −0.001 | 0.02 | 0.02 | 0.02 |
| 1 | 1.08 | 0.10 | 5.65 | 13.48 | 0.018 | 0.007 | 1.56 | 1.66 | 1.69 |
| 2 | 1.16 | 0.14 | 7.56 | 18.98 | 0.019 | 0.007 | 2.13 | 1.73 | 1.68 |
| 3 | 1.68 | 0.07 | 7.36 | 19.83 | 0.010 | 0.004 | 1.14 | 0.96 | 0.88 |
| 4 | 2.68 | 0.36 | 7.77 | 18.92 | 0.046 | 0.019 | 5.29 | 4.14 | 4.13 |
| 5 | 3.00 | 0.27 | 6.74 | 16.62 | 0.040 | 0.016 | 3.98 | 3.60 | 3.54 |
| 6 | 4.72 | 0.43 | 5.82 | 14.33 | 0.074 | 0.030 | 6.31 | 6.57 | 6.47 |
| 7 | 4.86 | 0.53 | 7.36 | 18.24 | 0.072 | 0.029 | 7.80 | 6.41 | 6.27 |
| 8 | 6.08 | 0.65 | 7.29 | 19.32 | 0.089 | 0.034 | 9.60 | 7.94 | 7.26 |
| 9 | 6.82 | 0.62 | 7.74 | 20.65 | 0.080 | 0.030 | 9.15 | 7.13 | 6.48 |
| 10 | 7.00 | 0.37 | 6.95 | 16.51 | 0.053 | 0.022 | 5.43 | 4.75 | 4.85 |
| 11 | 9.92 | 0.74 | 7.52 | 18.96 | 0.098 | 0.039 | 10.98 | 8.77 | 8.43 |
| 12 | 12.18 | 1.09 | 6.51 | 15.63 | 0.167 | 0.070 | 16.52 | 15.16 | 15.30 |
| 13 | 13.48 | 1.04 | 6.69 | 16.13 | 0.155 | 0.064 | 15.71 | 14.03 | 14.10 |

TABLE 2-continued

| | Hg | | | | | | | | |
|---|---|---|---|---|---|---|---|---|---|
| | Reference | Analysis | Control emission amount | | Hg corrected value | | Hg concentration-converted value | | |
| | measurement | emission | | | (276) | (351) | for $h_0$ | for $h_1$ | for $h_2$ |
| Sample # | value (ppb) ($X_H$) | amount ($h_0$) | (276) ($t_1$) | (351) ($t_2$) | ($h_1$ = $h_0/t_1$) | ($h_2$ = $h_0/t_2$) | ($H_0$) (ppb) | ($H_1$) (ppb) | ($H_2$) (ppb) |
| 14 | 14.36 | 1.03 | 8.25 | 22.64 | 0.125 | 0.045 | 15.55 | 11.18 | 9.85 |
| 15 | 19.60 | 1.60 | 7.88 | 18.47 | 0.203 | 0.087 | 25.22 | 18.58 | 19.23 |
| 16 | 22.50 | 1.41 | 6.55 | 16.10 | 0.215 | 0.088 | 21.88 | 19.78 | 19.45 |
| 17 | 34.44 | 2.50 | 7.92 | 18.11 | 0.316 | 0.138 | 43.18 | 30.09 | 31.99 |
| 18 | 35.70 | 2.21 | 6.62 | 16.19 | 0.334 | 0.137 | 36.92 | 32.06 | 31.59 |
| Correlation coefficient with $X_H$ (R) | | | | | | | $R_{H0}$ = 0.9841706 | $R_{H1}$ = 0.9878385 | $R_{H2}$ = 0.9854658 |

TABLE 3

| | Pb | | | | Pb corrected value | | Pb concentration-converted value | | |
|---|---|---|---|---|---|---|---|---|---|
| | Reference | Analysis | Control emission amount | | (276) | (351) | for $p_0$ | for $p_1$ | for $p_2$ |
| | measurement | emission | | | | | | | |
| Sample # | value (ppb) ($X_P$) | amount ($P_0$) | (276) ($t_1$) | (351) ($t_2$) | ($p_1$ = $p_0/t_1$) | ($p_2$ = $p_0/t_2$) | ($P_0$) (ppb) | ($P_1$) (ppb) | ($P_2$) (ppb) |
| 0 | 0.00 | 0.22 | 6.56 | 16.32 | 0.034 | 0.013 | 0.03 | 0.03 | 0.03 |
| 1 | 11.74 | 2.01 | 5.65 | 13.48 | 0.356 | 0.149 | 12.58 | 13.53 | 13.79 |
| 2 | 1.48 | 0.66 | 7.56 | 18.98 | 0.087 | 0.035 | 2.99 | 2.20 | 2.11 |
| 3 | 6.89 | 1.54 | 7.36 | 19.83 | 0.209 | 0.078 | 9.15 | 7.24 | 6.39 |
| 4 | 2.74 | 0.82 | 7.77 | 18.92 | 0.106 | 0.043 | 4.08 | 2.94 | 2.96 |
| 5 | 4.01 | 0.90 | 6.74 | 16.62 | 0.134 | 0.054 | 4.63 | 4.09 | 4.03 |
| 6 | 4.58 | 0.87 | 5.82 | 14.33 | 0.149 | 0.061 | 4.43 | 4.75 | 4.68 |
| 7 | 3.17 | 0.71 | 7.36 | 18.24 | 0.096 | 0.039 | 3.33 | 2.57 | 2.52 |
| 8 | 2.57 | 1.06 | 7.29 | 19.32 | 0.145 | 0.055 | 5.74 | 4.58 | 4.10 |
| 9 | 7.03 | 2.30 | 7.74 | 20.65 | 0.297 | 0.111 | 14.76 | 10.98 | 9.84 |
| 10 | 11.63 | 2.18 | 6.95 | 16.51 | 0.314 | 0.132 | 13.86 | 11.70 | 11.99 |
| 11 | 8.05 | 1.82 | 7.52 | 18.96 | 0.242 | 0.096 | 11.18 | 8.62 | 8.25 |
| 12 | 4.20 | 1.10 | 6.51 | 15.63 | 0.169 | 0.070 | 6.02 | 5.56 | 5.65 |
| 13 | 4.84 | 1.07 | 6.69 | 16.13 | 0.160 | 0.066 | 5.81 | 5.18 | 5.25 |
| 14 | 7.04 | 1.61 | 8.25 | 22.64 | 0.195 | 0.071 | 9.65 | 6.65 | 5.73 |
| 15 | 9.41 | 2.25 | 7.88 | 18.47 | 0.286 | 0.122 | 14.39 | 10.48 | 10.92 |
| 16 | 15.12 | 2.80 | 6.55 | 16.10 | 0.427 | 0.174 | 18.64 | 16.71 | 16.45 |
| 17 | 18.29 | 3.57 | 7.92 | 18.11 | 0.451 | 0.197 | 24.92 | 17.76 | 18.99 |
| 18 | 14.73 | 2.89 | 6.62 | 16.19 | 0.437 | 0.179 | 19.35 | 17.12 | 16.95 |
| Correlation coefficient with $X_P$ (R) | | | | | | | $R_{P0}$ = 0.9638074 | $R_{P1}$ = 0.9773404 | $R_{P2}$ = 0.9838003 |

Note that the identical samples were used for both Table 2 and Table 3, and thus the values for $t_1$ and $t_2$ are also the same.

As illustrated by Table 2, regarding the measurements for mercury, the correlation coefficient ($R_{H0}$) between the Hg reference measurement values ($x_H$) and the Hg concentration-converted values ($H_0$) based on the Hg analysis emission amounts ($h_0$) was 0.9841706. The correlation coefficient ($R_{H1}$) between $x_H$ and the Hg concentration-converted values ($H_1$) based on the Hg corrected values (276) ($h_1$) obtained by correcting $h_0$ using the control emission amounts (276) ($t_1$) was 0.9878385. Further, the correlation coefficient ($R_{H2}$) between $x_H$ and the Hg concentration-converted values ($H_2$) based on the Hg corrected values (351) ($h_2$) obtained by correcting $h_0$ using the control emission amounts (351) ($t_2$) was 0.9854658. Of these three correlation coefficients, $R_{H1}$ was the largest.

From the above results, it can be seen that for the measurements of mercury in the samples, the strongest correlation to reference measurement values was exhibited by the values obtained by correcting analysis emission amounts for mercury using control emission amounts respectively derived from an emission amount for thallium at a wavelength of 276 nm.

As illustrated by Table 3, regarding the measurements for lead, the correlation coefficient ($R_{P0}$) between the Pb reference measurement value ($x_P$) and the Pb concentration-converted values ($P_0$) based on the Pb analysis emission amounts ($p_0$) was 0.9638074. The correlation coefficient ($R_{P1}$) between $x_P$ and the Pb concentration-converted values ($P_1$) based on the Pb corrected values (276) ($p_1$) obtained by correcting $p_0$ using the control emission amounts (276) ($t_1$) was 0.9773404. Further, the correlation coefficient ($R_{P2}$) between $x_P$ and the Pb concentration-converted values ($P_2$) based on the Pb corrected values (351) ($p_2$) obtained by correcting $p_0$ using the control emission amounts (351) ($t_2$) was 0.9838003. Of these three correlation coefficients, $R_{P2}$ was the largest.

From the above results, it can be seen for the measurements of lead in the samples, the strongest correlation to reference measurement values was exhibited by the values obtained by correcting analysis emission amounts for lead using the control emission amounts respectively derived from an emission amount for thallium at a wavelength of 351 nm.

(5) Emission Spectrum of the Control Metal Species

Figure 5A:
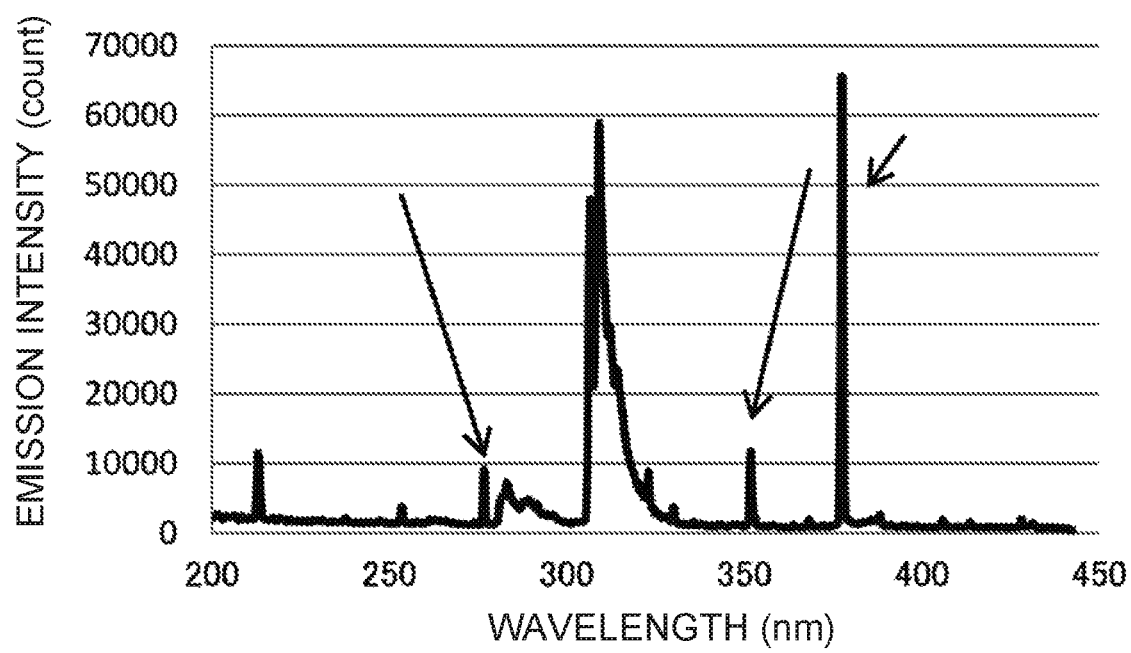
FIG. 5A illustrates an emission spectrum for thallium, which serves as a control metal species.
Figure 5B:
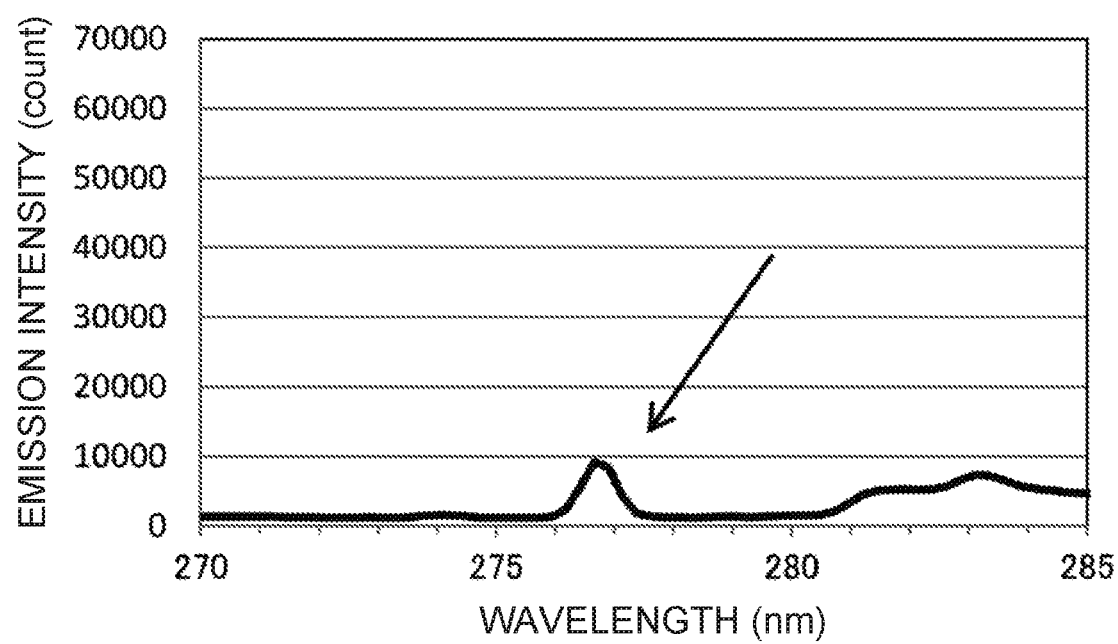
FIG. 5B is an enlargement of a characteristic peak in the vicinity of a control wavelength of 276 nm in FIG. 5A.
Figure 5C:
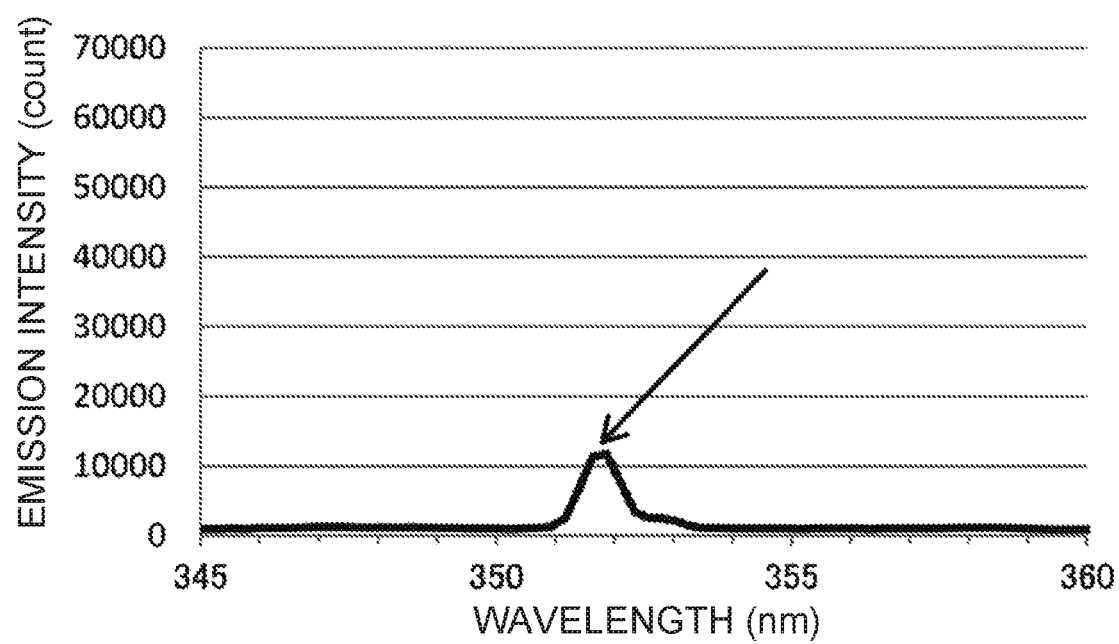
FIG. 5C is an enlargement of a characteristic peak in the vicinity of a control wavelength of 351 nm in FIG. 5A.
Figure 5D:
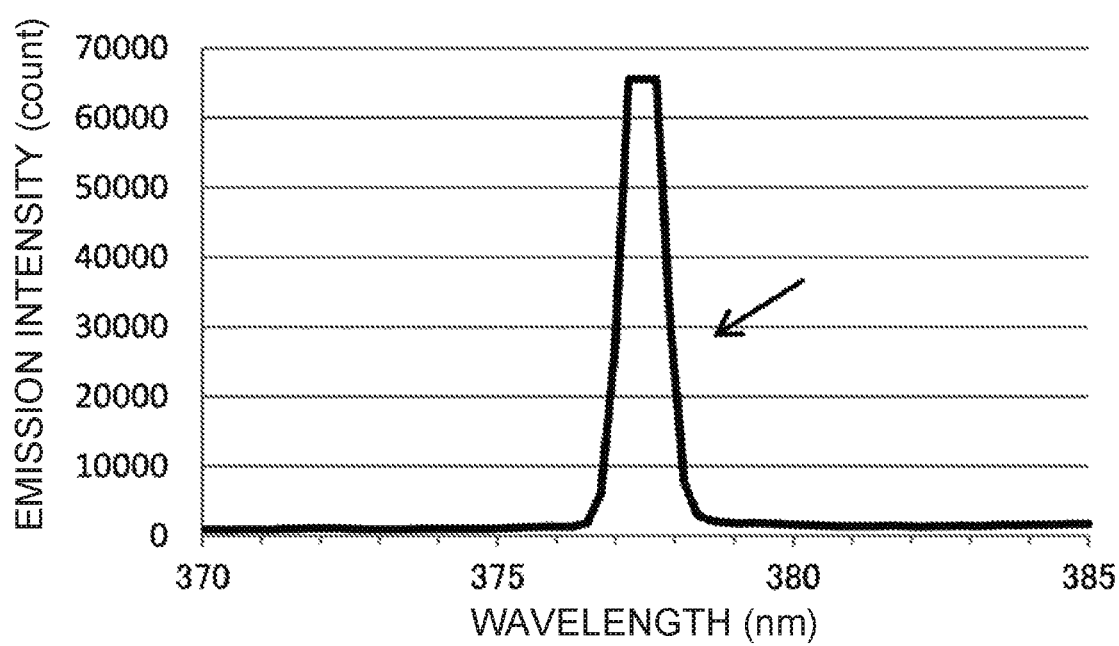
FIG. 5D is an enlargement of a characteristic peak in the vicinity of a control wavelength of 378 nm in FIG. 5A.

Note that the actual emission spectrum of thallium as the control metal species is illustrated in FIG. 5A. The characteristic peaks of the control wavelengths at three locations, indicated by arrows in FIG. 5A, can be used as control emission amounts. These are enlarged in FIG. 5B to FIG. 5D, respectively. Namely, the control wavelength for the characteristic peak illustrated in FIG. 5B is in the vicinity of 276 nm, and the characteristic peak at this control wavelength forms the basis for calculating the control emission amount (276) ($t_1$) suitable for measuring mercury, as described above. Moreover, the control wavelength for the characteristic peak illustrated in FIG. 5C is in the vicinity of 351 nm, and the characteristic peak at this control wavelength forms the basis for calculating the control emission amount (351) ($t_2$) suitable for measuring lead, as described above. Note that the control wavelength for the characteristic peak illustrated in FIG. 5D is in the vicinity of 378 nm. This could conceivably be used as the basis for calculating a control emission amount for another analyte metal species.

Emission spectra for zinc, cadmium, silver, gold, and indium, which are available for control metal species other than thallium, are illustrated in FIG. 6A and FIG. 6B, FIG. 7A and FIG. 7B, FIG. 8A and FIG. 8B, FIG. 9A and FIG. 9B, and FIG. 10A and FIG. 10B, respectively.

Figure 6A:
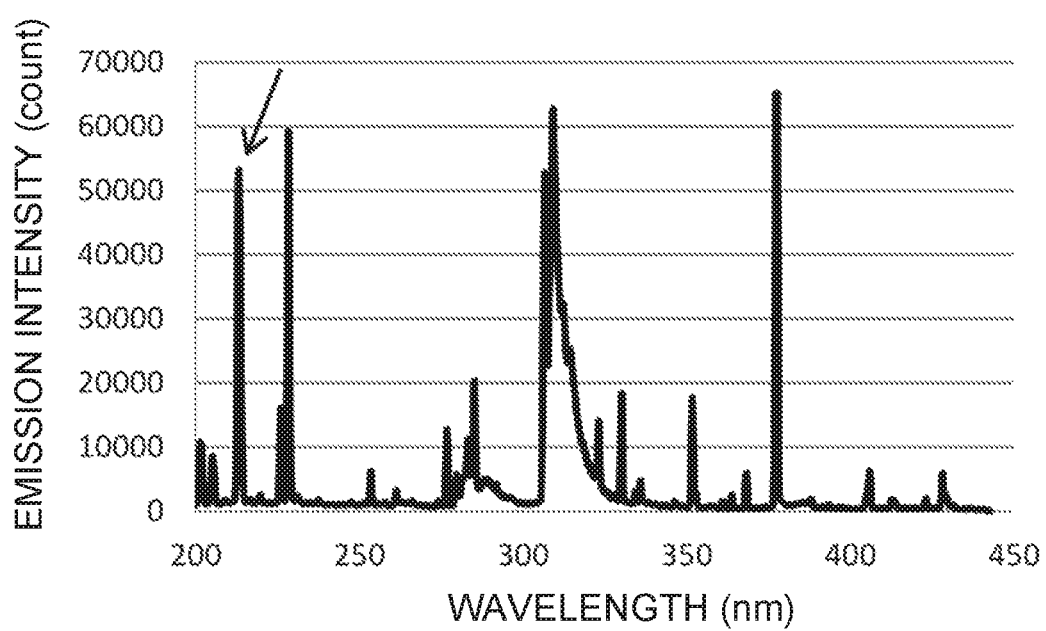
FIG. 6A illustrates an emission spectrum for zinc, which serves as a control metal species.
Figure 6B:
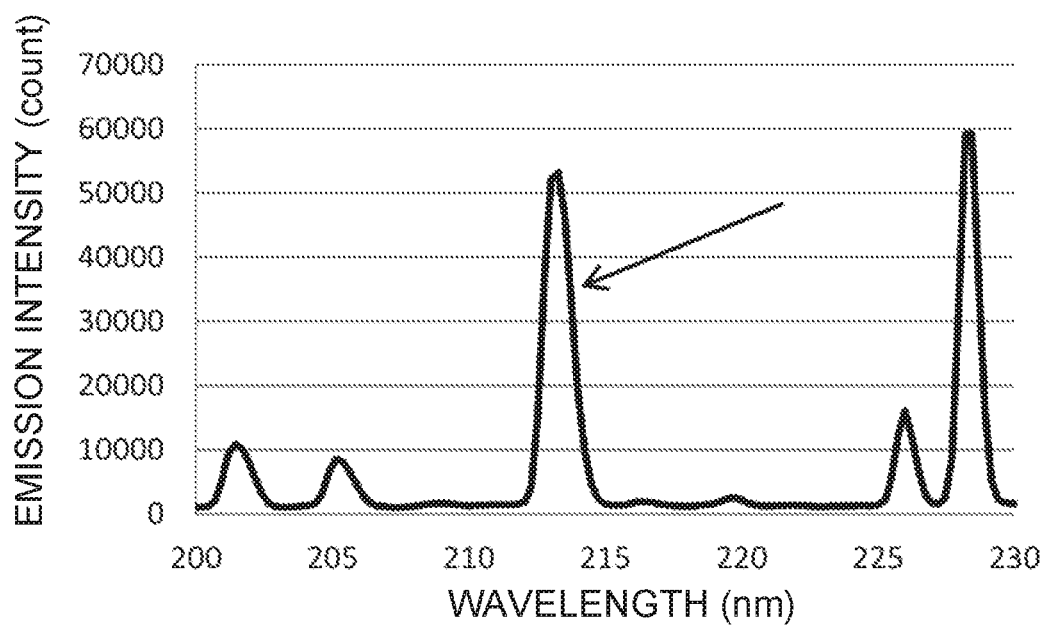
FIG. 6B is an enlargement of a characteristic peak of a control wavelength in the vicinity of 213 nm in FIG. 6A.

In the emission spectrum for zinc illustrated in FIG. 6A, a characteristic peak can be seen in the vicinity of the 213 nm wavelength (FIG. 6B), which may be used as a control wavelength.

Figure 7A:
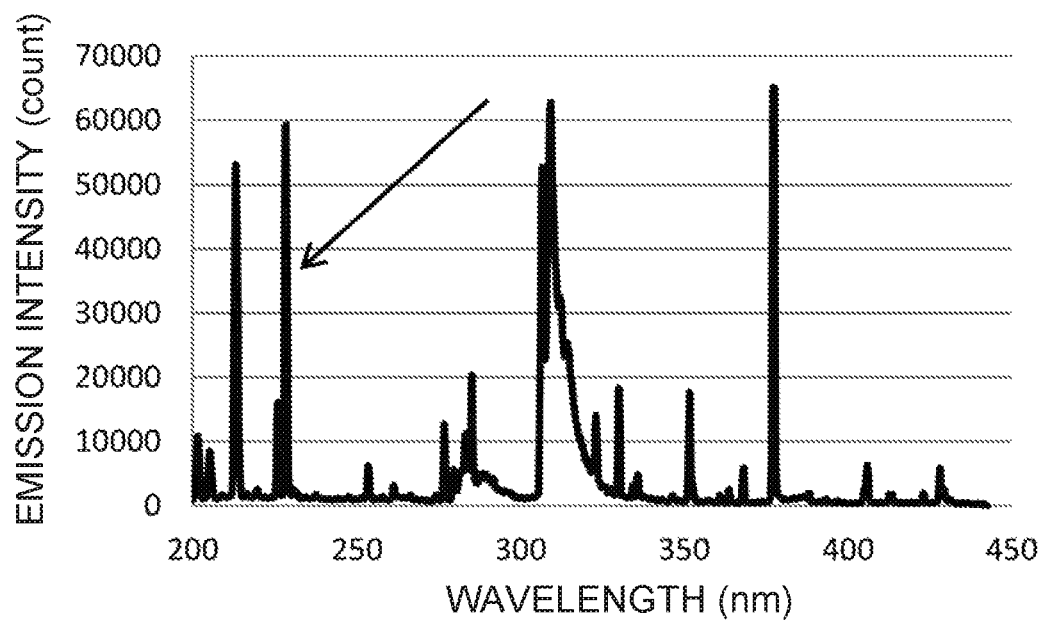
FIG. 7A illustrates an emission spectrum for cadmium, which serves as a control metal species.
Figure 7B:
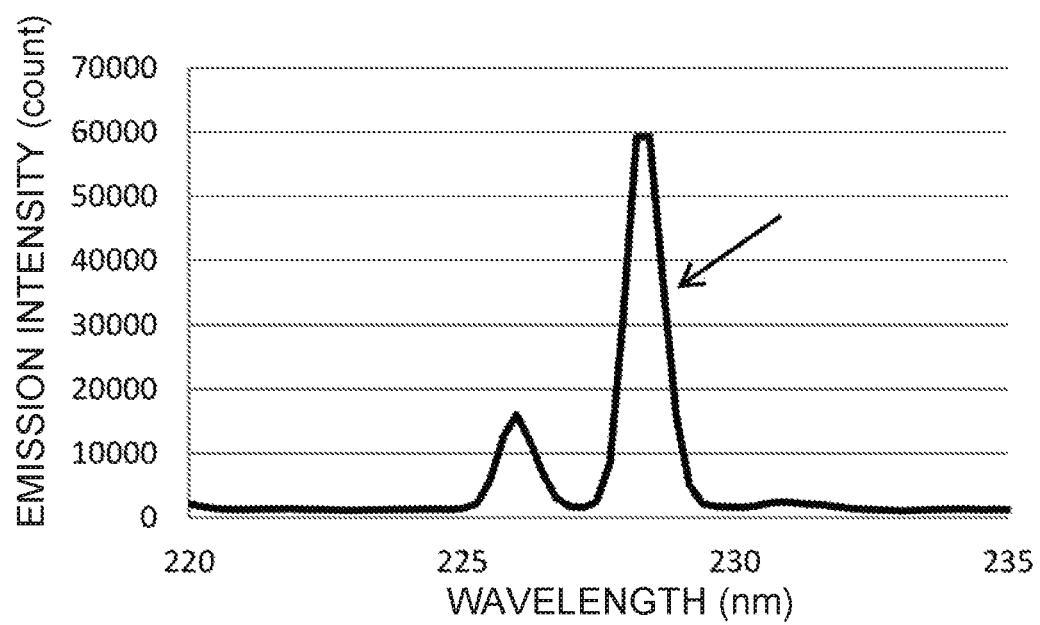
FIG. 7B is an enlargement of a characteristic peak of a control wavelength in the vicinity of 228 nm in FIG. 7A.

In the emission spectrum for cadmium illustrated in FIG. 7A, a characteristic peak can be seen in the vicinity of the 228 nm wavelength (FIG. 7B), which may be used as a control wavelength.

Figure 8A:
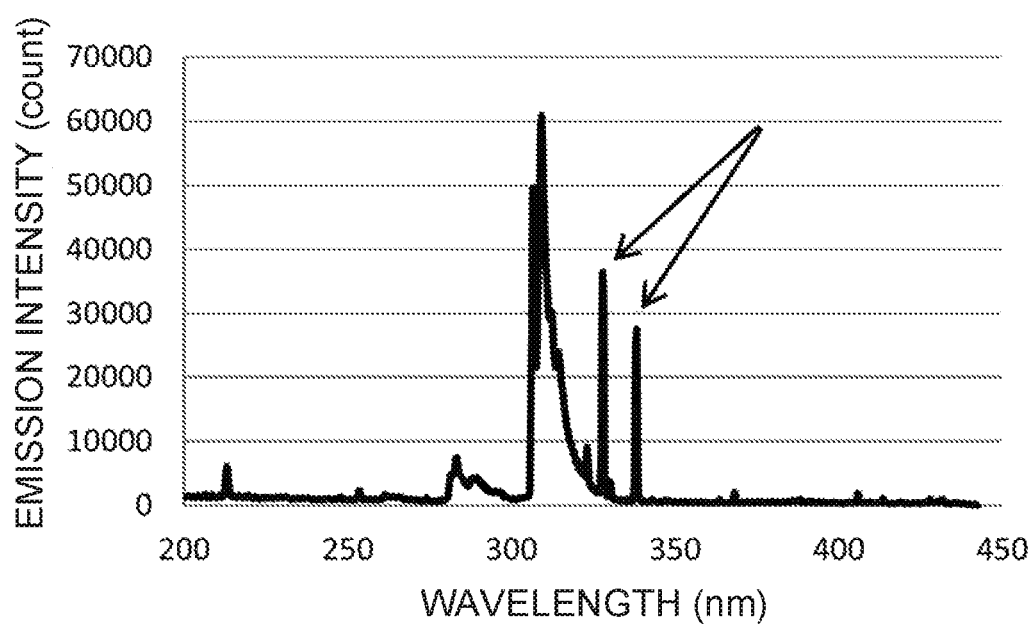
FIG. 8A illustrates an emission spectrum for silver, which serves as a control metal species.
Figure 8B:
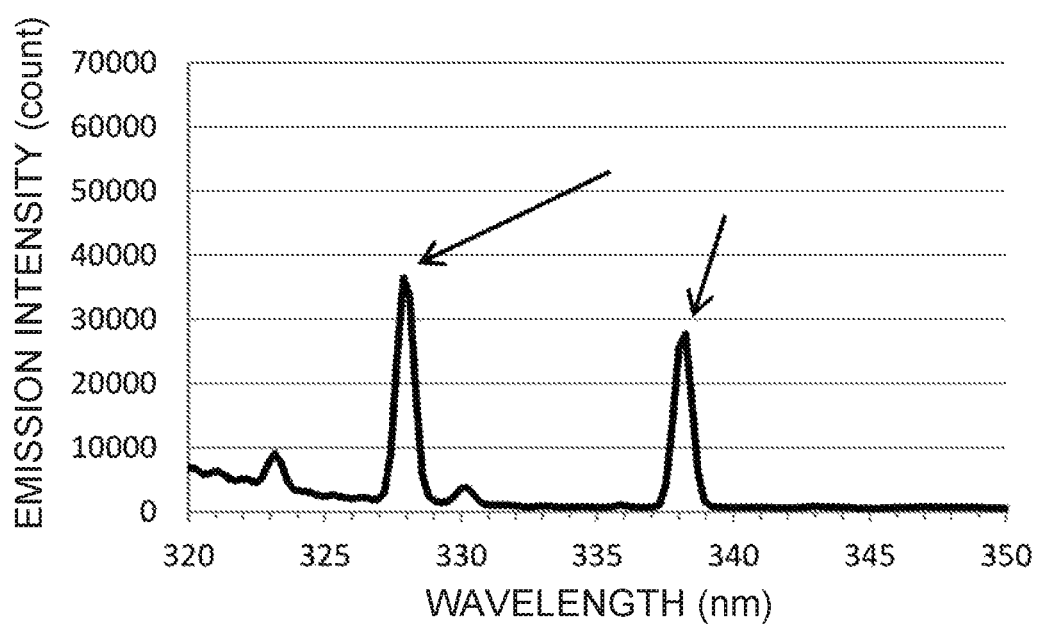
FIG. 8B is an enlargement of characteristic peaks of control wavelengths in the vicinity of 328 nm and in the vicinity of 338 nm in FIG. 8A.

In the emission spectrum for silver illustrated in FIG. 8A, characteristic peaks can be seen in the vicinity of the 328 nm wavelength and in the vicinity of the 338 nm wavelength (FIG. 8B), which may be used as control wavelengths.

Figure 9A:
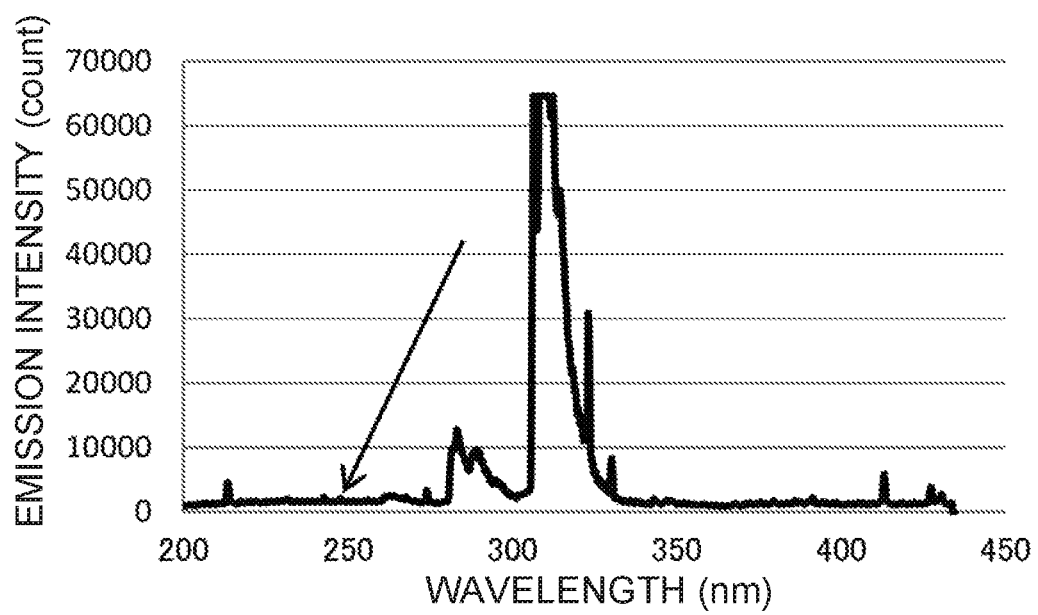
FIG. 9A illustrates an emission spectrum for gold, which serves as a control metal species.
Figure 9B:
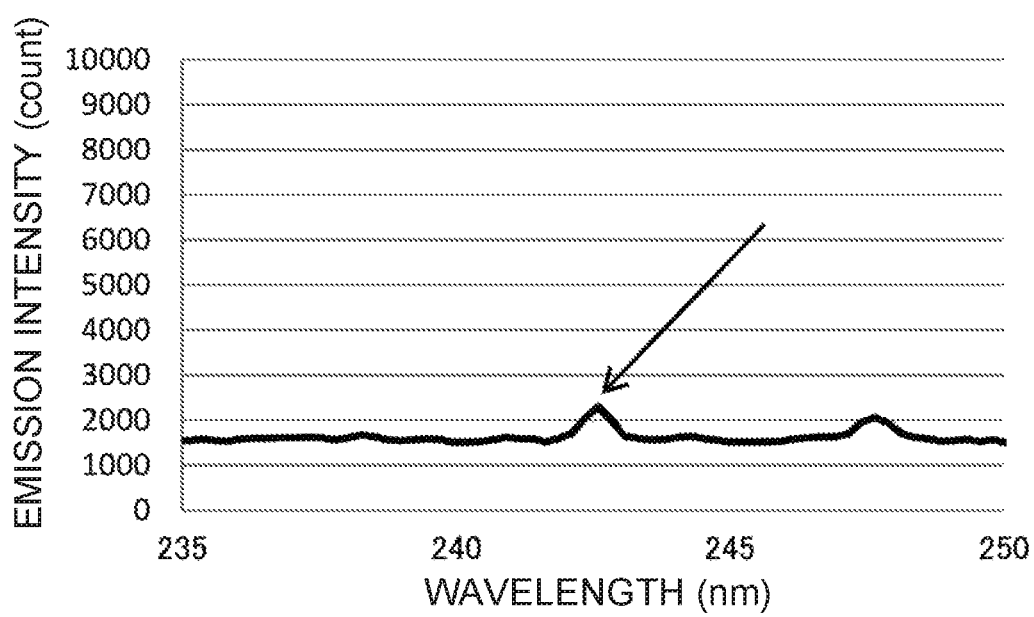
FIG. 9B is an enlargement of a characteristic peak of a control wavelength in the vicinity of 243 nm in FIG. 9A.

In the emission spectrum for zinc illustrated in FIG. 9A, a characteristic peak can be seen in the vicinity of the 243 nm wavelength (FIG. 9B), which may be used as a control wavelength.

Figure 10A:
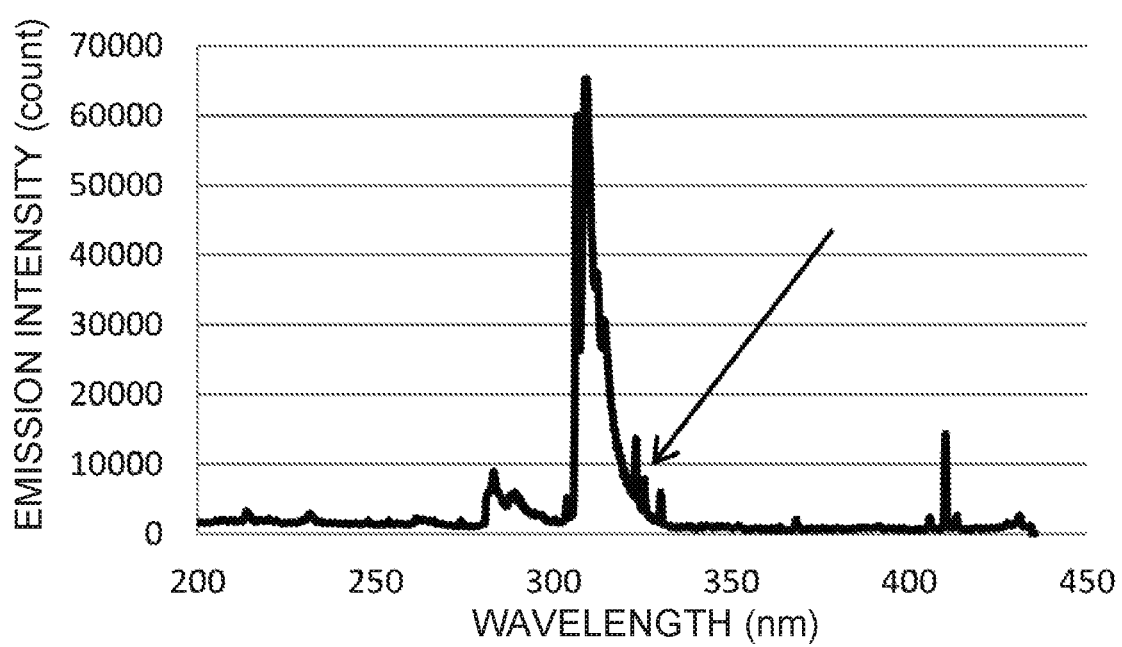
FIG. 10A illustrates an emission spectrum for indium, which serves as a control metal species.
Figure 10B:
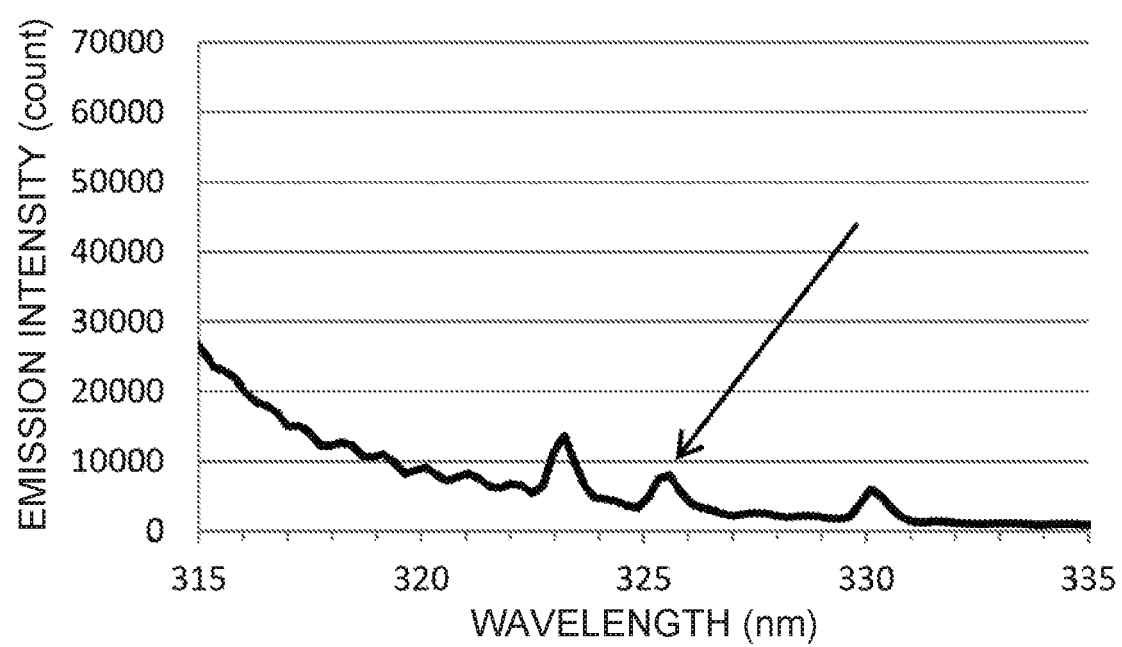
FIG. 10B is an enlargement of a characteristic peak of a control wavelength in the vicinity of 325 nm in FIG. 10A.

In the emission spectrum for indium illustrated in FIG. 10A, a characteristic peak can be seen in the vicinity of the 325 nm wavelength (FIG. 10B), which may be used as a control wavelength.

Moreover, mercury and lead, which served as the analyte metal species in the foregoing examples, may also be employed as control metal species with samples in which these metal species are not present. In such cases, as described above, the control wavelength for mercury is in the vicinity of 256 nm (see FIG. 4A), and the control wavelength for lead is in the vicinity of 368 nm (see FIG. 4B).

INDUSTRIAL APPLICABILITY

The present invention may be utilized in a method in which a heavy metal is concentrated on an electrode via stripping, and plasma emission is used to quantify the heavy metal.

What is claimed is:

1. A plasma spectroscopy analysis method comprising:
a preparatory process of adding a control metal species that is different from an analyte metal species to a sample so as to have a known concentration, the control metal species comprising at least one metal species selected from the group consisting of zinc, cadmium, silver, gold, thallium, and indium, and the analyte metal species comprising mercury and lead;
a concentration process of introducing the sample to a measurement container, and applying an electric current across a pair of electrodes disposed in the measurement container to concentrate the analyte metal species and the control metal species in the sample in a vicinity of at least one of the electrodes;
a detection process of applying an electric current across the pair of electrodes after the concentration process so as to generate plasma, and detecting emitted light from the analyte metal species and the control metal species arising due to the plasma;
a correction process of calculating a corrected value by correcting an analysis emission amount that is a net emission amount at an analysis wavelength corresponding to the analyte metal species detected in the detection process, using a control emission amount that is a net emission amount at a control wavelength corresponding to the control metal species detected in the detection process; and
a quantification process of quantifying the analyte metal species in the sample by comparing the corrected value to a calibration curve obtained by advance measurements of known concentrations of the analyte metal species.

2. The plasma spectroscopy analysis method of claim 1, wherein, in the correction of the correction process, a value obtained by dividing the analysis emission amount by the control emission is taken as the corrected value.

3. The plasma spectroscopy analysis method of claim 2, wherein the analyte metal species and the control metal species are able to exist in the sample in an ionized state.

4. The plasma spectroscopy analysis method of claim 1, wherein the control metal species is thallium.

5. The plasma spectroscopy analysis method of claim 1, wherein the control metal species is a metal species selected from the group consisting of zinc, cadmium, silver, gold, thallium, and indium.

6. The plasma spectroscopy analysis method of claim 1, wherein the analyte metal species consists of mercury and lead.

7. The plasma spectroscopy analysis method of claim 1, wherein the control metal species comprises thallium.

8. The plasma spectroscopy analysis method of claim 1, wherein the sample further comprises a chelating agent.

9. The plasma spectroscopy analysis method of claim 8, wherein the chelating agent is selected from the group consisting of dithizone, tiopronin, meso-2,3-dimercaptosuccinic acid (DMSA), sodium 2,3-dimercapto-1-propanesulfonic acid (DMPS), ethylenediaminetetraacetic acid (EDTA), nitrilotriacetic acid (NTA), ethylenediamine-N,N'-disuccinic acid (EDDS), and α-lipoic acid.

10. The plasma spectroscopy analysis method of claim 1, wherein the sample further comprises a masking agent.

11. The plasma spectroscopy analysis method of claim 1, wherein the masking agent is selected from the group consisting of maleimide, N-methylmaleimide, N-ethylmaleimide, N-phenylmaleimide, maleimidopropionic acid, iodoacetamide, and iodoacetate.

12. The plasma spectroscopy analysis method of claim 1, wherein a concentration voltage applied during the concentration process is at least 1 mV.

13. The plasma spectroscopy analysis method of claim 1, wherein a concentration voltage applied during the concentration process is at least 400 mV.

14. The plasma spectroscopy analysis method of claim 1, wherein the electric current during the concentration process is applied from 0.2 minutes to 40 minutes.

15. The plasma spectroscopy analysis method of claim 1, wherein the electric current during the concentration process is applied from 5 minutes to 20 minutes.

16. The plasma spectroscopy analysis method of claim 1, wherein a plasma generation voltage applied during the detection process is at least 10V.

17. The plasma spectroscopy analysis method of claim 1, wherein a plasma generation voltage applied during the detection process is at least 100V.

18. The plasma spectroscopy analysis method of claim 1, wherein the electric current across the electrodes during the detection process is larger than that during the concentration process.

19. The plasma spectroscopy analysis method of claim 1, wherein the electric current across the electrodes during the detection process is from 0.01 mA to 100,000 mA.

20. The plasma spectroscopy analysis method of claim 1, wherein the electric current across the electrodes during the detection process is from 50 mA to 2,000 mA.

* * * * *